United States Patent [19]

Stokley

[11] Patent Number: 4,976,698
[45] Date of Patent: Dec. 11, 1990

[54] INTRAVENOUS CATHETER AND TUBING STABILIZATION DEVICE

[76] Inventor: Manuel H. Stokley, Rte. 2, Box 144-D, Winnsboro, Tex. 75494

[21] Appl. No.: 111,584

[22] Filed: Oct. 23, 1987

[51] Int. Cl.$^5$ .............................................. A61M 5/32
[52] U.S. Cl. ................................... 604/174; 604/180; 128/DIG. 6; 128/DIG. 26
[58] Field of Search ................ 604/93, 180, 174, 179; 128/DIG. 6, DIG. 26, 132 R, 134, 133

[56] References Cited

U.S. PATENT DOCUMENTS

| | | | |
|---|---|---|---|
| 3,194,235 | 7/1965 | Cooke | 128/132 R |
| 3,812,851 | 5/1974 | Rodriguez | 128/DIG. 6 |
| 3,901,227 | 8/1975 | Klatskin | 128/DIG. 6 |
| 3,942,528 | 3/1976 | Loeser | 128/DIG. 26 |
| 4,029,103 | 6/1977 | McConnell | 128/DIG. 26 |
| 4,453,933 | 6/1984 | Speaker | 128/DIG. 26 |
| 4,517,971 | 5/1985 | Sorbonne | 128/DIG. 6 |
| 4,561,857 | 12/1985 | Sacks | 128/DIG. 6 |
| 4,679,553 | 7/1987 | Proulx et al. | 128/DIG. 6 |
| 4,711,636 | 12/1987 | Bierman | 604/180 |

*Primary Examiner*—John D. Yasko
*Attorney, Agent, or Firm*—Ronald B. Sefrna

[57] ABSTRACT

A device for securing and stabilizing an intravenous catheter and a portion of its associated tubing in place relative to the limb of a patient, comprising a planar base to be removeably attached to the limb of a patient adjacent the catheter entry site, having a pair of U-shaped walls defining an acruate slot therebetween to receive and stabilize the catheter tubing, and further having a cover adapted to be removeably interconnected to the planar base to retain and stabilize the catheter and associated tubing relative to the limb of the patient and prevent direct access to the catheter entry site. The device is preferably constructed of a clear plastic material and is preferably attached to the limb of the patient with one or more flexible adhesive strips.

18 Claims, 2 Drawing Sheets

INTRAVENOUS CATHETER AND TUBING STABILIZATION DEVICE

FIELD OF THE INVENTION

The present invention generally relates to means of securing an intravenous catheter and tubing in use with a patient, and more particularly related to a device for securing and stabilizing an intravenous catheter and associated tubing adjacent to the site of entry of the catheter through the skin of the patient, protecting the catheter and its entry site from interference, and facilitating access to the catheter for maintenance by medical personnel while minimizing physical trauma to the patient.

BACKGROUND OF THE INVENTION

Intravenous infusion of fluids and intravenous removal of fluids has been and continues to be a common practice in the medical treatment and care of patients in hospitals and other medical facilities. A typical intravenous infusion system comprises a catheter penetrating the skin and an underlying vein of, most commonly, the patient's arm, a source of fluid, and tubing interconnecting the source of fluid and the infusion catheter. In order to minimize movement of the needle or catheter relative to the limb of the patient and to prevent inadvertant removal of the catheter, it is standard practice to secure the catheter and a portion of its associated tubing to the limb of the patient. With conventional methods of medical practice, a needle-bearing catheter is inserted through the skin of the patient into an underlying vein, the needle is removed and the catheter is secured to the skin of the patient with adhesive tape. In addition to securing the catheter, a portion of the associated tubing is looped or coiled and similarly secured to the patient's skin with several strips of adhesive tape for the purpose of absorbing anY tension imposed upon such tubing without displacing the catheter. While this conventional system has proven to be reasonably effective in securing the catheter and tubing, it has several disadvantages.

First, the process of initially securing the catheter and tubing with several strips of adhesive tape is a cumbersome and time consuming process for the medical personnel. Further, it is necessary, if the intravenous treatment is to be continued for any extended period of time, to periodically check the catheter and tubing and to inspect the catheter entry site, and to periodically change the tubing interconnecting the catheter to the source of infusion fluid. In each instance the tape securing the intravenous infusion components to the limb of the patient must be removed and replaced strip bY strip; a process which is both time consuming for the medical personnel and painful for the patient. Second, the use of flexible adhesive tape to secure the catheter to the limb of the patient does not fully protect either the catheter or the tubing from displacement or constriction as a result of movement of the patient or impingement of other objects against the catheter or tubing. Third, the flexible adhesive tape does not prevent flexing of the patient's limb in the area of the catheter entry site and thus is ineffective in maintaining the proper alignment of the catheter relative to its entry site or to the vein into which fluid is being infused.

Several attempts have been made in the prior art in an effort to overcome these and other disadvantages of the conventional approach. One approach has been to provide a device for attachment to the limb of the patient for the purpose of retaining a loop of tubing, exemplified by U.S. Des. Pat. No. 290,041 to Scott, U.S. Pat. No. 3,942,528 to Loeser, U.S. Pat. No. 4,029,103 to McConnell, and U.S. Pat. No. 4,453,933 to Speaker. This approach, while helpful to a degree in securing the tubing, does not improve the protection or stabilization of the catheter and does not fully aleviate the use of adhesive tape to secure the catheter and tubing.

Another approach has been to additionallY provide some catheter support in addition to tubing retention, as illustrated by U.S. Pat. No. 3,918,446 to Buttaravoli, U.S. Pat. No. 4,397,641 to Jacobs, and U.S. Pat. No. 4,449,975 to Perry. While reflecting some improvement over the previous system, this approach has still failed to shield the catheter from impingement by other objects or from tampering, and has failed to adequately address problems which may arise from flexing of the patient's limb at the catheter entry site.

SUMMARY OF THE INVENTION

The present invention provides a device designed and constructed to retain and stabilize an intravenous catheter and a portion of its associated tubing so as to isolate the catheter from tension imposed on its associated tubing, to protect the catheter and its entry site from impingement of other objects, to restrict flexing of the patient's limb in the vacinity of the catheter entry site, and to eliminate the steps of removal and replacement of multiple strips of adhesive tape associated with inspection and replacement of the intravenous tubing. The device of the invention is also useful in retaining and protecting an intravenous catheter without attached tubing, a configuration often used to provide a readily available entry site for the intravenous administration of medication or rapid connection of a source of infusion fluid.

The device of the invention generally comprises a planar base component to be removeably attached to the limb of the patient, and a rigid cover component to be removeably interconnected to said base. The base component of the device includes a pair of U-shaped walls disposed near one end of such base and extending upwardly from the plane of the base to form an arcuate slot therebetween to receive a portion of the tubing associated with the intravenous catheter. In the preferred embodiment, the base of the device includes a wide portion upon which said U-shaped walls are disposed and an elongate narrow portion integrally interconnected thereto. In the preferred embodiment of the device, the base is provided with an adhesive strip at each end thereof for attachment to the limb of the patient.

The cover component of the device of the invention comprises an elongate body having a length substantially equal to the length of the base of the device, and a width substantially equal to the width of the wide portion of said base, designed to be placed over said base and removeably interconnected thereto. The cover includes an elongate top with an integrally formed side wall extending substantially perpendicular to said face along both long sides and one end thereof. When the cover is interconnected to the base of the device a passageway is formed through one end of the combined device and through the arcuate slot defined by said walls to receive and retain the portion of the intravenous tubing adjacent to the catheter, and the cover is configured to firmly retain the hub or body of the catheter relative to the limb of the patient.

The base and cover of the device are preferably constructed of inexpensive transparent plastic materials and are capable of being sterilely packaged as a disposable unit for ease of use and protection against contamination.

DETAILED DESCRIPTION OF THE INVENTION

Figure 1:
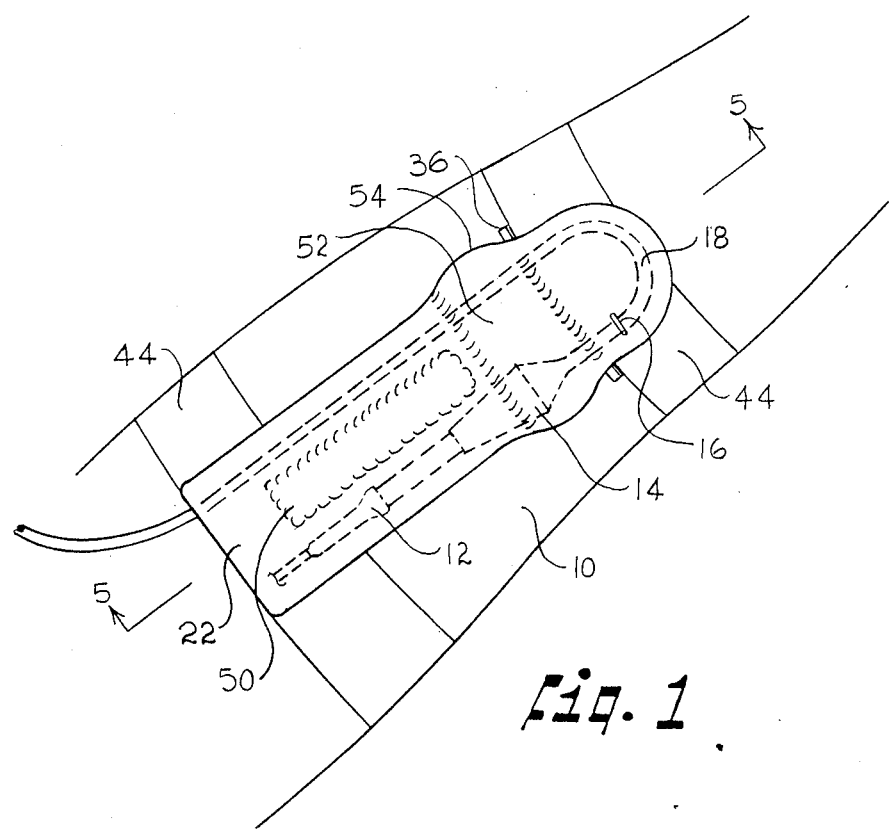
FIG. 1 is a perspective view of the device of the invention, illustrating a typical use of the device in place upon the arm of a patient.

A more detailed description of the device of the invention will now be provided with reference to the accompanYing drawing figures. Referring first to FIG. 1, the intravenous catheter and tubing stabilization device of the invention, generally indicated by reference numeral 10, is used to anchor and stabilize a catheter 12, with catheter hub assembly 14 and tubing coupler 16, and to retain tubing 18 associated therewith. Tubing 18 may be connected to a source of infusion fluid (not shown), or may be connected to a fluid receiver (not shown) for use when fluid is being withdrawn from a patient. AlternativelY, device 10 may be used to anchor and protect a catheter 12 without tubing 18 attached thereto, a configuration sometimes used to provide an entry site for intravenous infusion of medication or other fluids.

Figure 2:
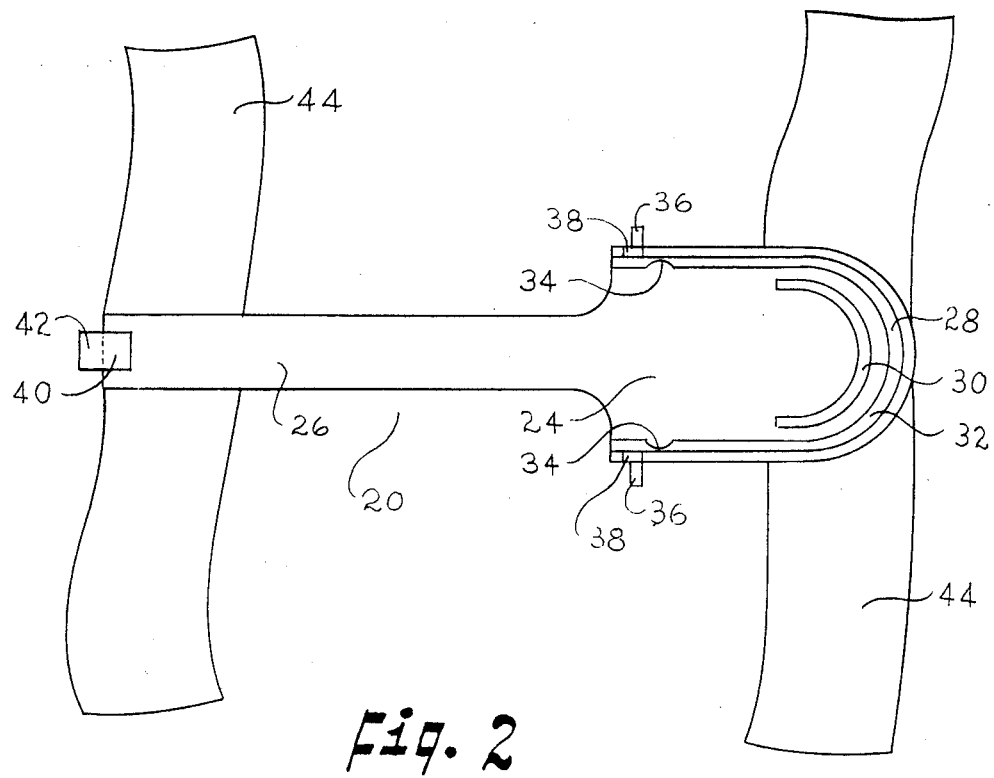
FIG. 2 is a plan view of the base component of the device of the invention.
Figure 3:
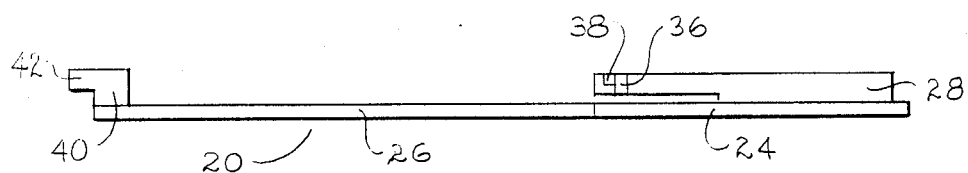
FIG. 3 is a side elevation view of the base component of the device of the invention, omitting adhesive strips for claritY.
Figure 4:
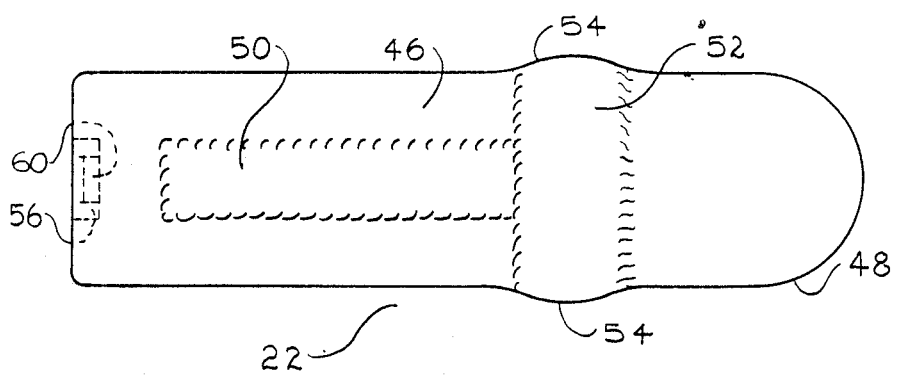
FIG. 4 is a plan vIew of the cover component of the device of the invention.
Figure 5:
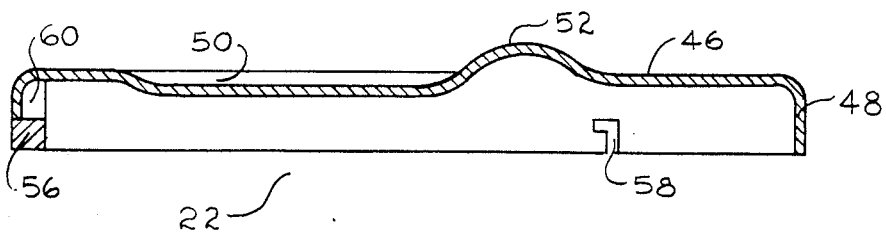
FIG. 5 is cross-sectional elevation view of the cover component of the device of the invention along line 5—5 of FIG. 1.

With further reference to the drawing figures, catheter and tubing stabilization device 10 includes a base 20 depicted in FIGS. 2 and 3, and a cover 22, depicted in FIGS. 4 and 5. Base 20 comprises an elongate plate of generally spade-like configuration, having a wide portion 24 and a narrow elongate portion 26 integrally interconnected at one end to one edge of portion 24 with a smoothly curving intersection, and with the longitudinal axis of portion 26 in alignment with the longitudinal axis of portion 24. The side and rear edges of portion 24 define a smooth convex curvature to eliminate sharp corners which might cause injury to the skin of a patient with whom device 10 is to be used. Base 20 further includes a first U-shaped wall 28 disposed on portion 24 in perpendicular relation thereto, and a second U-shaped wall 30 similarly disposed on portion 24 of base 20 in such relation to wall 28 to define arcuate slot 32 between said walls to receive tubing 18 therein. The curvature of walls 28 and 30 substantially matches the curvature of the edges of portion 24. The distance between wall 28 and wall 30 through slot 32 should be substantially equal to the cross-sectional diameter of tubing 18 so that tubing 18 will be frictionally retained in slot 32 without constricting the flow of fluid through such tubing. Wall 28 is of greater length than wall 30 and, in the preferred embodiment depicted in the drawing figures, extends to the edge of portion 24 of base 20.

Wall 28 preferably includes opposed notches 34 extending into its inner surface near the edge of portion 24, to receive tubing coupler 16 therein for anchoring the catheter assembly in relation to the limb of the patient. The parts of wall 28 extending beyond the ends of wall 30 toward the edge of portion 24 are not connected to portion 24 of base 20, and wall 28 should be constructed of a slightly flexible but shape retentive material to allow those parts of wall 28 to be deformed from their rest position with imposition of force thereon, but return to such rest position upon removal of such force.

Base 20 additionally includes locking ears 36 interconnected to the outer surface of wall 28 in perpendicular relation thereto, in opposed relationship across the longitudinal axis of base 20. Locking ears 36 are of the same height as wall 28 and extend outwardly therefrom beyond the respective edges of portion 24 a short distance, and each is disposed on the outer surface of wall 28 between its respective end and the position of each of notches 34 in the inner surface of wall 28. Locking tabs 38 are disposed between locking ears 36 and the ends of wall 28, in the corners formed at the intersection of ears 36 and wall 28, and are interconnected between ears 36 and wall 28. Locking tabs 38 are of essentially cubical configuration with an edge dimension approximately equal to or slightly greater than the thickness of side wall 48 of cover 22.

Base 20 still further includes connector block 40 disposed on the end of the narrow rectangular portion 26 of base 20 opposite its interconnection to portion 24 and interconnected thereto such that connector block 40 extends from the surface of base 20 in the same direction as walls 28 and 30. Connector block 40 comprises a solid block of generally rectangular cross-section having a tab 42 extending outwardly therefrom toward the end of portion 26 of base 20 opposite the interconnection of portion 26 and portion 24. Base 20 also includes patient attachment means 44 which, in the preferred embodiment, comprises a pair of wide adhesive strips interconnected to base 20 at opposite ends thereof with the longitudinal axes of such strips mutually perpendicular to the longitudinal axis of base 20. The one of patient attachment means 44 disposed at the end of portion 26 of base 20 is of sufficient width to overlie the entry site of catheter 12 during use of device 10 to aid in anchoring catheter 12 and protecting its entry site against contamination.

Base 20 is preferably molded as a one piece construction from a hard, smooth surfaced plastic material capable of being suitably sterilized for medical use. Portion 26 of base 20 is preferably slightly flexible perpendicular to the plane of base 20, to facilitate positioning of base 20 on a limb of a patient adjacent to a catheter inserted therein, and the parts of wall 28 free from interconnection to portion 24 of base 20 must be sufficiently flexible to allow bending awaY from their rest positions while sufficiently shape retentive to return to their rest positions upon removal of the bending force.

Cover 22 of device 10, depicted in FIG. 4 and FIG. 5, is of substantially the same length as base 20 and of substantially the same width as wide rectangular portion 24 of base 20. Cover 22 comprises an elongate top 46 with a side wall 48 extending continuously around both sides and one end of top 46 and interconnected thereto in perpendicular relationship. The other end of top 46, and thus of cover 22, is open to allow passage of tubing 18 to the interior of device 10. Side wall 48 is preferably integrally interconnected to top 46 with a smoothly rounded intersection between side wall 48 and top 46 to prevent snagging of tubing 18 and injury to the patient to which the device is attached. The end of top 46 interconnected to side wall 48 is of convex curvature matching the curvature of wall 28 of base 20.

Top 46 of cover 22 includes elongate depression 50 formed therein with its longitudinal axis parallel to the longitudinal axis of cover 22, and further includes dome 52 formed therein with its longitudinal axis perpendicular to the longitudinal axis of cover 22. Depression 50 is disposed in cover 22 such that depression 50 is centered over portion 26 of base 20 with cover 22 placed on base 20. Dome 52 is positioned in cover 22 adjacent to one end of depression 50 such that dome 52 will overlie that part of portion 26 of base 20 immediately adjacent to the interconnection of portions 24 and 26 of base 20. Dome 52 is slightly longer along its longitudinal axis than the width of top 46 and extends outward beyond the line of the edge of top 46 on both sides thereof in the preferred embodiment. Side wall 48 includes bulges 54 under the extension of dome 52 beyond the edges of top 46. Depression 50, dome 52, and bulges 54 are provided for the purpose of accomodating and retaining catheter hub assembly 14. Base 20 and cover 22 of device 10 are symmetrical about the longitudinal axis of device 10 to allow device 10 to be used with catheter 12 on either side of the device.

Cover 22 further includes connector means for forming a releaseable interconnection between cover 22 and base 20. Such connector means comprise connector plate 56 interconnected to the edge of top 46 at the open end of cover 22, centered between the ends of wall 48 and extending from top 46 in the same direction as wall 48, and locking slots 58 disposed in side wall 48 between bulges 54 and the curved end of cover 22 in opposed relationship across the longitudinal axis of cover 22. Connector plate 56 includes aperture 60 extending from the inner face of plate 56 into the interior thereof toward the open end of cover 22, to receive tab 42 of base 20. Each of locking slots 58 comprises an L-shaped aperture extending through side wall 48, disposed therein such that the first leg of the L extends upward from the bottom edge of side wall 48 toward top 46 and the second leg of the L extends perpendicular to the first leg toward the open end of cover 22. Locking slots 58 are disposed in cover 22 so as to overlie locking ears 36 and locking tabs 38 when cover 22 is placed over base 20.

Cover 22 is preferably formed as a one piece molded construction of a rigid, smooth surfaced plastic material capable of being suitably sterilized for medical use. All external contours of cover 22 should be smooth and rounded to prevent snagging of tubing 18 and to prevent patient injury. In the preferred embodiment, cover 22 is transparent to allow inspection of the catheter components and tubing and of the catheter entry site without the necessity of removing cover 22 from base 20, but cover 22 and base 20 may be translucent or colored if desired without departing from the scope of the invention. Device 10 is designed to be provided to users as an individually packaged sterile, disposable unit.

In use of device 10 to stabilize and retain an intravenous catheter and its tubing in conjunction with the intravenous infusion of fluid to or removal of fluid from a patient, a needle bearing catheter, such as illustrated by reference numeral 12, is inserted through the skin of the patient and into an underlying vein, the needle is withdrawn and catheter hub assembly 14 and intravenous tubing 18 are connected to catheter 12. Base 20 of device 10 is placed on the skin of the patient adjacent to catheter 12, with portion 26 of base 20 alongside catheter 12 and with tubing coupler 14 resting upon portion 24 of base 20 and received in one of notches 34 of wall 28. Base 20 is then attached to the patient by, in the preferred embodiment, adhering adhesive strips 44 to the skin of the patient with one of said strips lying over the entry site of catheter 12 through the skin of the patient. Tubing 18 is inserted into slot 32 between walls 28 and 30 of base 20 and is drawn toward the opposite end of base 20 along the edge of portion 26 opposite catheter 12.

Cover 22 is then interconnected to base 20 by first placing aperture 60 of connector plate 56 over tab 42 of connector block 40 and pressing cover 22 onto base 20 such that locking ears 36 are received in locking slots 58. As cover 22 is pressed onto base 20 the pressure of the bottom edge of side wall 48 against locking tabs 38 forces the ends of wall 28 to bend toward the interior of device 10, allowing cover 22 to be brought into full contact with base 20, whereupon locking tabs 38 slide into locking slot 58 as the ends of wall 28 return to their rest position, firmly locking cover 22 in place upon base 20. In addition, as cover 22 is pressed onto base 20, the inner surface of side wall 48 along its curvature is brought into contact with the outer surface of a portion of wall 28 of base 20, aiding the frictional retention of cover 22 upon base 20. As cover 22 is brought into full interconnection with base 20, dome 52 and one of bulges 54 in side wall 48 enclose and gently retain catheter hub assembly 14 relative to device 10, thus retaining catheter 12 in proper alignment wIth its entry sIte. The placement of tubing coupler 16 within notch 34 in wall 28 restrains longitudinal movement of catheter hub assembly 14 and thus of catheter 12 connected thereto.

Visual inspection of catheter 12, hub assembly 14, and tubing 18, as well as visual inspection of the catheter entry site, can be readily performed without removal of the transparent cover 22 and without any discomfort to the patient. Direct access to catheter 12, hub assembly 14, and tubing 18 is achieved by pressing inward on the ends of locking ears 36 which extend outwardly beyond side wall 48 of cover 22 to release locking tabs 38 from slots 58, and lifting cover 22 away from base 20, eliminating the painful and time consuming process of removing and replacing strips of adhesive tape.

The foregoing detailed description of a specific embodiment of the device of the invention is illustrative and not for purposes of limitation, and it will be understood that various modifications and adaptations may be made without departing from the spirit and scope of the invention.

What is claimed is:

1. A device for anchoring and stabilizing a catheter and a portion of its associated tubing relative to a patient, comprising:
   a base to be positioned upon the skin of a patient adjacent to a catheter inserted through such skin, said base having a pair of elongate curved wall members, each having first and second ends, with said wall members interconnected to the surface of said base in proximity to each other so as to define an arcuate slot therebetween to receive a portion of the tubing associated with the catheter and frictionally retain said tubing without restricting the flow of fluid therethrough to effectively isolate said tubing from the catheter associated therewith;

a substantially rigid cover, with first and second ends, to be positioned over said base and releaseably interconnected thereto to anchor and retain said catheter relative to the skin of the patient and to cover and enclose said catheter and the tubing retained within said arcuate slot, said cover having an opening at one end thereof for routing of tubing associated with said catheter therethrough and away from the patient;

connector means for releaseably interconnecting said cover to said base; and attachment means for removeably attaching said base to the skin of the patient.

2. The device of claim 1, wherein said base comprises:

an elongate plate, with first and second ends and upper and lower faces, having a wide first portion extending from the first end of said plate toward the second end of said plate and a narrow second portion extending from said first portion to said second end of said plate in coaxial alignment with said first portion;

a first wall member, having first and second ends, disposed in U-shaped curvature on and extending outwardly from the upper face of said first portion with said ends of said first wall member extending toward said second end of said plate, and interconnected to said upper face through a part of the length of said first wall member intermediate its ends;

a second wall member, having first and second ends, disposed in U-shaped curvature on and extending outwardly from said upper face of said first portion nearer the center of said first portion from said first wall member with said ends of said second wall member extending toward said second end of said plate, and interconnected to said upper face of said first portion;

an open ended arcuate slot between and defined by said first and second wall members to receive a portion of the tubing associated with said catheter; and connector means for releaseably interconnecting said cover of said device of said base.

3. The device of claim 1, wherein said cover comprises:

an elongate substantially planar top of substantially the same length as said base and of substantially the same width throughout the length of aid top as the widest portion of said base, having a dome transversely formed therein and extending upwardly from the plane of said top with its longitudinal axis perpendicular to the longitudinal axis of said top to receive and firmly retain the catheter relative to said cover;

a side wall extending downwardly from the plane of said top around two long sides and the end of said top at the first end of said cover, and interconnected to said top perpendicular to the plane of said top; and connector means to releaseably interlock with connector means of the base of said device to allow said cover to be releaseably interconnected to the base of said device.

4. The device of claim 1, wherein said attachment means for removeably attaching the base of the device to the skin of a patient comprises one or more flexible strips each interconnected on one side to the surface of said base to be placed against the skin of the patient and coated on the opposite side with an adhesive compound for adhering said one or more flexible strips to the skin of the patient.

5. A device for anchoring and stabilizing an intravenous catheter and a portion of its associated tubing relative to a patient, comprising:

an elongate substantially planar base with first and second ends and upper and lower faces, of a length greater than the length of the catheter and any catheter hub assembly connected between said catheter and the tubing associated therewith, having a wide portion extending from the first end of said base toward said second end through a part of the length of said base and smoothly narrowing to a narrow portion extending to said second end of said base with its longitudinal axis in alignment with the longitudinal axis of said wide portion;

a first elongate wall member with first and second ends, disposed in a U-shape on the upper face of said wide portion of said base with said ends of said first wall member extending in the direction of said second end of said base, said first wall member being interconnected to said wide portion of said base along the central portion of said first wall member intermediate its ends, leaving the ends and adjacent portions of said first wall member free from interconnection to said base;

a second elongate wall member with first and second ends, disposed in a U-shape on said upper face of said wide portion of said base a short distance toward the center of said wide portion from said first wall member, with the ends of said second wall member extending in the same direction as the ends of said first wall member, and interconnected to said wide portion of said base through the full length of said second wall member;

an arcuate slot defined between said first and second wall members to receive a portion of the tubing associated with the catheter and frictionally retain said tubing therein;

an elongate cover with two sides and first and second ends, to be releaseably interconnected to said base, having a substantially planar top including a transverse dome formed in said top intermediate its two ends with the longitudinal axis of said dome perpendicular to the longitudinal axis of said top, further including an elongate depression formed in said top between said dome and the second end of said top with the longitudinal axis of said depression aligned with the longitudinal axis of said top, and having a side wall disposed perpendicular to the plane of said top, extending from the two sides and the first end of said top generally perpendicular thereto in a direction opposite the extension of said dome therefrom and interconnected to said top along the full length of said side wall;

first connector means for releaseably interconnecting said cover to said base, disposed between said first and second ends of said cover and of said base;

second connector means for releaseably interconnecting said cover to said base, disposed at second ends of said cover and of said base; and attachment means for removeably attaching said base to the skin of the patient adjacent to the site of entry of the catheter through the skin of the patient.

6. The device of claim 5, wherein said first end of said base is rounded in convex curvature and said first end of said cover is rounded in convex curvature with a radius of curvature substantially equal to the radius of curvature of the first end of said base.

7. The device of claim 5, wherein the ends of said first wall member are aligned with the edge of said wide portion of said base nearest the second end of said base, and wherein said second wall member is of shorter length than said first wall member and the ends of said second wall member do not extend to the edge of said wide portion of said base.

8. The device of claim 5, wherein the heights of said first wall member and of said second wall member above the upper face of said base and the height of said side wall of said cover from its interconnection to the top of said cover are substantially equal.

9. The device of claim 5, wherein said first wall member includes one or more notches to receive a portion of a hub assembly of a catheter, each of said on or more notches extending into the interior of said wall member from the surface thereof nearer the center of said wide portion of said base through the full height of said wall member near the end or ends thereof, and, if more than one, said notches being disposed in substantially equally divided opposing relationship across the longitudinal axis of said base.

10. The device of claim 5, wherein the ends of said transverse dome of said cover extend beyond the sides of the planar portion of the top of said cover and the side wall of said cover curves outward under the extension of the ends of said dome to form opposing bulges in said side wall underlying the ends of said transverse dome.

11. The device of claim 5, wherein the distance from the first end of said cover to the beginning of said transverse dome of said cover is substantially equal to the distance from the first end of said base to the edge of said wide portion of said base nearest the second end of said base.

12. The device of claim 5, wherein said first connector means for releaseably interconnecting said cover to said base comprises:
a pair of locking ears of substantially the same height as said first wall member of said base, each interconnected to said first wall member near one end thereof in opposed relationship across the longitudinal axis of said base and extending outwardly from said first wall member beyond the sides of said wide portion of said base, having a pair of interlock tabs of shorter length and height than said locking ears, each extending on the surface of aid first wall member from each said locking ear toward said second end of said base in alignment with the upper edge of said locking ear; and
a pair of L-shaped slots in said side wall of said cover, each having a first leg extending from the lower edge of said side all of said cover toward the top of said cover to receive one of said locking ears, and a second leg extending from said first leg toward the second end of said cover to receive one of said interlock tabs therein, with said L-shaped slots disposed in said side wall in opposed relation across the longitudinal axis of said cover and positionin in said side wall such that each said L-shaped slot is aligned with a different one of said locking ears and interlock tabs when said cover is aligned with said base.

13. The device of claim 5, wherein said second connector means for releaseably interconnecting said cover to said base comprises:
a connector block laterally centered upon and interconnected to the upper face of said base at its second end, extending from said base in the same direction as said wall members, and having a ledge extending from said connector block beyond said second end of said base parallel to the plane of said base; and
a connector plate laterally centered upon and interconnected to the lower surface of the top of said cover at its second end, extending downward therefrom in the same direction as said side wall, and having an aperture extending into said connector plate from its inner face in the direction of said second end of said cover to receive the ledge of said connector block therein.

14. The device of claim 5, wherein said attachment means for removeably attaching the base of said device to the skin of a patient comprises one or more thin flexible strips, each interconnected on one side to the lower face of said base and coated on the opposite side with an adhesive material to adhere said strips to the skin of a patient.

15. The device of claim 5, wherein said attachment means for removeably attaching the base of said device to the skin of a patient comprises two elongate thin flexible air permeable strips, each interconnected on one side to the lower face of said base and coated on the opposite side with an adhesive material suitable for adhesion of said strip to the skin of a patient, one of said strips being interconnected to the lower face of said base near the first end of said base with the longitudinal axis of said strip perpendicular to the longitudinal axis of said base, and the other of said strips being interconnected to the lower face of said base near the second end of said base with its longitudinal axis perpendicular to the longitudinal axis of said base and extending from said second end of said base toward said first end of said base a sufficient distance to overlie the entry site of the catheter to be anchored and stabilized by said device when said device is positioned upon the patient.

16. The device of claim 5, wherein said base and said first wall member are constructed of a slightly flexible shape retentive plastic material having a smooth surface finish and capable of being sterilized.

17. The device of claim 5, wherein said cover is constructed of a substantially rigid transparent plastic material having a smooth surface finish and capable of being sterilized.

18. The device of claim 5, wherein said cover is translucent.

* * * * *